United States Patent [19]

Deinhammer et al.

[11] Patent Number: 4,585,863
[45] Date of Patent: Apr. 29, 1986

[54] PROCESS FOR THE MANUFACTURE OF 2-ISOPROPYL-4-METHYL-6-HYDROXYPYRIMIDINE

[75] Inventors: Wolfgang Deinhammer; Bernd Schilling, both of Burghausen, Fed. Rep. of Germany

[73] Assignee: Wacker-Chemie GmbH, Munich, Fed. Rep. of Germany

[21] Appl. No.: 641,329

[22] Filed: Aug. 16, 1984

[30] Foreign Application Priority Data

Dec. 8, 1983 [DE] Fed. Rep. of Germany ....... 3344429

[51] Int. Cl.$^4$ ........................................... C07D 239/02
[52] U.S. Cl. .................................................... 544/319
[58] Field of Search ......................................... 544/319

[56] References Cited

U.S. PATENT DOCUMENTS

| 4,012,506 | 3/1977 | Balke et al. | 544/319 |
| 4,163,848 | 8/1979 | Blackwell, III et al. | 544/319 |

FOREIGN PATENT DOCUMENTS

| 2065698 | 12/1974 | Fed. Rep. of Germany. |
| 2853887 | 7/1980 | Fed. Rep. of Germany. |
| 2907773 | 9/1980 | Fed. Rep. of Germany. |
| 43-3363 | 2/1968 | Japan. |

OTHER PUBLICATIONS

Tetsuzo et al., Chem. Abst. 69-67123k (1968)., eq. JP. 3363.
Tetsuzo et al., Chem. Abst. 83-10126y (1975), eq. DE 2065698.
Schillig; Chem. Abst. 93-185796a eq. DE 2853887.
Schilling, Chem. Abst. 94-84157h eq. DE 2907773.

*Primary Examiner*—Mark L. Berch
*Assistant Examiner*—Cecilia Shen
*Attorney, Agent, or Firm*—Collard, Roe & Galgano

[57] ABSTRACT

An improved process for the manufacture of 2-isopropyl-4-methyl-6-hydroxypyrimidine, starting from 3-aminocrotonic acid amide and an acylating agent, without isolating the intermediately formed 3-isobutyrylaminocrotonic acid amide. In a first process step, the acylation is carried out with excess isobutyric acid anhydride in the presence of an alkali metal salt of isobutyric acid at temperatures of from 50° to 120° C. and in the absence of a solvent. In a second process step, the cyclization is carried out in the resulting reaction mixture by the addition of an aqueous alkali metal hydroxide solution at temperatures of from 80° to 105° C., and then the hydroxypyrimidine is isolated in known manner. The total quantities of alkali metal hydroxide added in the second process step are such that they are sufficient both for the neutralization of the isobutyric acid present in the reaction mixture and also for the cyclization. Less than 1 mole of alkali metal hydroxide per mole of the 3-aminocrotonic acid amide originally used is used for the cyclization itself.

3 Claims, No Drawings

PROCESS FOR THE MANUFACTURE OF 2-ISOPROPYL-4-METHYL-6-HYDROXYPYRIMIDINE

The present invention relates to a process for the manufacture of 2-isopropyl-4-methyl-6-hydroxypyrimidine of the formula

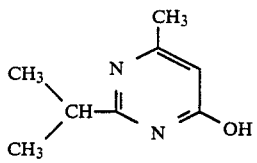

(abbreviated hereinafter as "hydroxypyrimidine"), which is required as an intermediate for obtaining 0,0-diethyl-0-(2-isopropyl-4-methylpyrimidin-6-yl) thionophosphate, which is commercially available as a fast-acting contact insecticide under the name "diazinon", are known. In addition to the normal industrial manufacturing process which is effected essentially by means of an expensive 4-step synthesis (known as the "amidine process"), a method of synthesis starting from 3-aminocrotonic acid amide, which is readily obtainable from diketene and ammonia, should be economically advantageous.

Although processes using the latter synthesis method have been amply described in patent literature, they have apparently not previously been carried out on an industrial scale. For example, 3-aminocrotonic acid amide has been reacted with isobutyric acid anhydride in approximately stoichiometric quantities, by heating under reflux in a chloroform solution, with the formation and isolation of 3-isobutyrylaminocrotonic acid amide, which can subsequently be cyclized under basic conditions to form hydroxypyrimidine (cf. JP-AS No. 6803.363, ref. in Chem. Abs. 69 (1968), page 6263).

The yields obtained when using that process are, however, very moderate. They are given as 62% of the theoretical yield for the first process step, and as 46% of the theoretical yield including the cyclization step. The reaction of 3-aminocrotonic acid amide has therefore been carried out with isobutyric acid isobutyl ester in the presence of sodium isobutoxide; this reaction, carried out as a one-pot process without the isolation of intermediates, results directly in hydroxypyrimidine (cf. DE-OS No. 20 65 698).

In addition, a one-pot process is known, which uses diketene and ammonia as starting materials, and in which the 3-aminocrotonic acid amide formed as intermediate is also cyclized with isobutyric acid butyl ester in the presence of sodium isobutoxide in toluene or in isobutanol solution until hydroxypyrimidine is obtained in the form of the sodium salt, from which the compound is liberated by the addition of acid, with yields of up to 88% (cf. U.S. Pat. No. 4,052,397).

Since the cyclization of the intermediately formed 3-isobutyrylaminocrotonic acid amide to form hydroxypyrimidine takes place with 1 mole of water being split off, which promotes the decomposition of the alcoholate and the resulting sodium hydroxide solution causes the hrydrolysis of the ester component, both the alkali metal alcoholate and also the ester must be used in considerable excess which is very uneconomical when carrying out such processes on an industrial scale.

Attempts have therefore been made to manufacture 3-isobutyrylaminocrotonic acid amide by acylation with dimethyl ketene (cf. DE-OS No. 28 53 887) and then to use the isolated compound in a one-pot process for the manufacture of diazinon, with the cyclization being carried out with excess, aqueous or alcoholic, sodium hydroxide solution, and the hydroxypyrimidine formed as the sodium salt then being reacted in suspension with a phosphorus compound (cf. DE-OS No. 29 07 773).

The use of dimethyl ketene as an acylating agent is, however, not only uneconomical, since isobutyric acid anhydride is required for its manufacture, but also dangerous since, as is known, alkyl ketenes have a tendency to form explosive peroxides. In addition, the isolation of 3-isobutyrylaminocrotonic acid amide always causes problems since this compound is thermolabile and is not sufficiently stable either in the acid range or in the alkaline range.

The problem is therefore to provide a process which, in a simpler and more economic manner than the processes known hitherto permits the manufacture of hydroxypyrimidine from 3-aminocrotonic acid amide and an acylating agent, without having to isolate the intermediately formed 3-isobutyrylaminocrotonic acid amide.

In the process for the manufacture of 2-isopropyl-4-methyl-6-hydroxypyrimidine by acylating 3-aminocrotonic acid amide with an isobutyryl compound, subsequently cyclizing the product under alkaline conditions and liberating the compound by means of an acid from the resulting hydroxypyrimidine derivative in the form of an alkali metal salt, this problem is solved according to the invention in that, in a first process step, the acylation is carried out with excess isobutyric acid anhydride in the presence of an alkali metal salt of isobutyric acid at temperatures of from 50° to 120° C. with the exclusion of a solvent and, in a second process step, the cyclization is carried out in the resulting reaction mixture by adding an aqueous alkali metal hydroxide solution at temperatures of from 80° to 105° C., and then the hydroxypyrimidine is isolated in a manner known, per se.

For the acylation in the first process step, it is possible to use from 1.01 to 1.5 moles, preferably from 1.05 to 1.3 moles, of isobutyric acid anhydride and from 0.01 to 0.4 moles, preferably from 0.02 to 0.15 moles, of the alkali metal salt of isobutyric acid per mole of 3-aminocrotonic acid amide. Especially suitable as alkali metal salts of isobutyric acid are potassium and sodium isobutyrate, the latter being preferred because it is more readily available.

In the second process step, an aqueous alkali metal hydroxide solution, preferably sodium hydroxide solution, is used, the concentration of which may be in the range of from 5 to 60% by weight, preferably from 10 to 50% by weight.

Furthermore, in the second process step, the total quantity of alkali metal hydroxide added is advantageously such that it is sufficient both for the neutralization of the isobutyric acid formed during the acylation reaction and resulting from the decomposition of excess isobutyric acid anhydride and also for the cyclization. Less than 1 mole of alkali metal hyrdroxide per mole of the 3-aminocrotonic acid amide originally used is required for the cyclization reaction itself, from 0.3 to 0.8 moles of alkali metal hydroxide per mole of the 3-aminocrotonic acid amide originally used, that is to say, in the first process step, being sufficient.

To carry out the process according to the invention, in the first process step, a mixture of isobutyric acid anhydride and alkali metal isobutyrate is advantageously heated and the 3-aminocrotonic acid amide is added to that mixture while the phases are mixed thoroughly and the temperature is maintained. The acylation reaction is complete after approximately from 0.25 to 10 hours, depending on the temperature chosen; generally, from approximately 0.5 to 2 hours is sufficient in the case of temperatures in the range of from 60° to 100° C.

Immediately after acylation has been completed, the aqueous alkali metal hydroxide solution for the second process step is introduced, without cooling and with vigorous mechanical agitation, into the resulting reaction mixture, which is already at reaction temperature, the isobutyric acid present being neutralized and cyclization to form the hydroxypyrimidine derivative being achieved. At the specified temperatures of from 80° to 105° C., the cyclization reaction is almost complete after approximately from 0.5 to 5 hours.

It is, however, also possible to carry out the process in such a manner that, after completion of the acylation reaction in the first process step, a portion of the isobutyric acid formed or of the excess isobutyric acid anhydride is removed by distillation under reduced pressure so that, in total, smaller quantities of the alkali metal hydroxide solution are necessary for the subsequent cyclization and neutralization in the second process step. As a result, considerable quantities of liquid can be saved when carrying out the process on an industrial scale, which leads to an improved space/time yield.

The further working-up to obtain the free hydroxypyrimidine can be carried out in a manner known, per se. For this purpose, the cooled reaction mixture is neutralized with a mineral acid, such as aqueous hydrochloric acid. The resulting solid can be separated off by centrifugation and washed with water. The mother liquor contains, in addition to the alkali metal isobutyrate, a small quantity of hydroxypyrimidine which can be recovered by extraction with water-immiscible organic solvents, such as methylene chloride, chloroform, 1,2-dichloroethane, benzene, toluene or xylene. It is, however, also possible to extract the entire suspension formed after the addition of acid, with one of the above-mentioned solvents and to isolate the hydroxypyrimidine after concentrating the extracts by evaporation. The hydroxypyrimidine obtained in that manner is generally sufficiently pure but can if necessary be even further purified by recrystallization. By the further addition of acid, the isobutyric acid can be liberated from the alkali metal isobutyrate present in the aqueous phase after the hydroxypyrimidine has been separated off and it can be isolated by separating the layers.

According to the process of the invention, yields of 2-isopropyl-4-methyl-6-hydroxypyrimidine of at least 90% of the theoretical yield, based on the 3-aminocrotonic acid amide used, are obtained.

The invention will now be explained more fully in a number of examples which are, however, only given by way of illustration and not of limitation.

EXAMPLE 173.8 g (1.1 moles) of isobutyric acid anhydride and 10 g (0.09 moles) of sodium isobutyrate are placed in a reaction vessel having a capacity of 1 liter and are heated to 80° C. While the mixture is stirred and occasionally cooled, 100 g (1.0 mole) of 3-aminocrotonic acid amide are introduced into this mixture sufficiently slowly for the temperature not to rise above 85° C. When the addition is complete, stirring is continued for 30 minutes while the temperature is maintained.

230 ml of a 25% by weight sodium hydroxide solution are then added (corresponding to a total of 1.84 moles of NaOH; allowing for the quantity used for neutralizing the isobutyric acid present, 0.64 moles of NaOH per mole of the 3-aminocrotonic acid amide used is available for the cyclization) and the reaction mixture is heated for 1 hour under reflux.

The reaction mixture is then cooled and neutralized with 20% by weight of hydrochloric acid. The resulting solid is filtered off by suction, washed with a little water, and dried. 116.2 g of 2-isopropyl-4-methyl-6-hydroxypyrimidine are obtained.

The mother liquors and washing liquors are extracted by shaking several times with methylene chloride. The extract is counter-extracted by shaking once with water. After distilling off the solvent 20.8 g of 2-isopropyl-4-methyl-6-hydroxypyrimidine remain, which corresponds to a total yield of 90.1% of the theoretical yield, based on the 3-aminocrotonic acid amide used.

While only several embodiments and examples of the present invention have been described, it is obvious that many changes and modifications may be made thereunto, without departing from the spirit and scope of the invention.

What is claimed is:

1. In a process for the manufacture of 2-isopropyl-4-methyl-6-hydroxypyrimidine by acylating 3-aminocrotonic acid amine with an isobutyryl compound, subsequently cyclizing the product under alkaline conditions and liberating the compound by means of an acid from the resulting hydroxypyrimidine derivative in the form of an alkali metal salt, the improvement comprising:

firstly, carrying out the acylation with excess isobutyric acid anhydride in the presence of an alkali metal salt of isobutyric acid at temperatures of from 50° to 120° C. in the absence of a solvent, wherein 1.01 to 1.5 moles of isobutyric acid anhydride and 0.01 to 0.4 moles of the alkali metal salt of isobutyric acid are used respectively per mole of 3-aminocrotonic acid amine;

secondly, carrying out the cyclization in the resulting reaction mixture by adding from 0.3 to 0.8 moles of aqueous alkali metal hydroxide solution at temperatures of from 80° to 105° C.; and isolating said hydroxypyrimidine obtained by said cyclization step.

2. The process of claim 1, wherein in the second process step, an aqueous alkali metal hydroxide solution having a concentration of from 10 to 50% by weight is used.

3. The process of claim 1, wherein in the second process step, the total quantity of alkali metal hydroxide added is such that it is sufficient both for the neutralization of the isobutyric acid formed during the acylation and resulting from the decomposition of excess isobutyric acid anhydride and also for the cyclization.

* * * * *